United States Patent [19]

Slettenmark et al.

[11] Patent Number: 5,344,432

[45] Date of Patent: Sep. 6, 1994

[54] IMPLANTABLE MEDICAL DEVICE AND METHOD FOR THE MANUFACTURE THEREOF

[75] Inventors: Bruno Slettenmark, Jaerfaella; Hans Strandberg, Sundyberg; Paul Brand, Boelsta, all of Sweden

[73] Assignee: Siemens Aktiengesellschaft, Munich, Fed. Rep. of Germany

[21] Appl. No.: 932,771

[22] Filed: Aug. 20, 1992

[30] Foreign Application Priority Data

Aug. 20, 1991 [DE] Fed. Rep. of Germany ....... 4127533

[51] Int. Cl.$^5$ ............................................... A61N 5/00
[52] U.S. Cl. ............................................................. 607/36
[58] Field of Search .................... 128/419 D; 607/5, 4

[56] References Cited

U.S. PATENT DOCUMENTS

| | | |
|---|---|---|
| 4,041,956 | 8/1977 | Purdy et al. . |
| 4,127,134 | 11/1978 | Ushakoff ........................ 128/419 P |
| 4,174,424 | 11/1979 | Jurva et al. . |
| 4,353,048 | 10/1982 | DeLucia . |
| 5,131,388 | 7/1992 | Pless et al. ...................... 128/419 D |

FOREIGN PATENT DOCUMENTS

| | | |
|---|---|---|
| 0434463 | 6/1991 | European Pat. Off. . |
| OS2931112 | 2/1981 | Fed. Rep. of Germany . |
| 2648275 | 12/1990 | France . |
| PS136104 | 6/1979 | German Democratic Rep. . |
| 55099713 | 1/1979 | Japan . |

OTHER PUBLICATIONS

"Ein Herzschrittmacher mit 10 Jahren Betriebsdauer," Mauser et al., Elektronik 1978, vol. 13, pp. 81–86.

*Primary Examiner*—Kyle L. Howell
*Assistant Examiner*—Marianne Parker
*Attorney, Agent, or Firm*—Hill, Steadman & Simpson

[57] ABSTRACT

An implantable medical device, such as a heart pacemaker, or defibrillator, has a welded capsule housing which is filled with a gas mixture containing helium, the helium permitting the detection of leaks in the capsule housing. To improve the electrical insulating properties, the remaining gas of the mixture is selected from a group of gases having electrically insulating properties, such as nitrogen, sulfur hexafluoride, carbon dioxide, or halogenated hydrocarbons.

2 Claims, No Drawings

IMPLANTABLE MEDICAL DEVICE AND METHOD FOR THE MANUFACTURE THEREOF

BACKGROUND OF THE INVENTION

1. Field of the Invention

The present invention is directed to an implantable medical device of the type having a welded capsule housing which is filled with a gas mixture, and to a method for manufacturing such a device.

2. Description of the Prior Art

In known heart pacemakers, the pacemaker electronics is arranged in a hermetically closed capsule housing, which is filled with a gas mixture of helium and argon. As disclosed, for example, in U.S. Pat. No. 4,174,424, helium is especially well suited for detecting leaks in the capsule housing, due to its extremely small molecules. Argon, by contrast, is preferably employed as a protective gas when welding the capsule housing, as disclosed in U.S. Pat. No. 4,041,956. The known helium-argon gas mixture, however, has relatively poor electrical insulating properties.

A method for manufacturing a film capacitor having a capsule housing filled with an insulating gas such as sulfur hexafluoride, nitrogen or carbon dioxide is disclosed in Japanese Application 55 099 713. A capsule housing for ultra-high frequency circuits whose parts are welded together in a helium-nitrogen atmosphere is disclosed in French Patent 2 648 275. Neither of these publications, however, is directed to an solving the aforementioned problems in the context of an implantable medical device.

SUMMARY OF THE INVENTION

It is an object of the present invention to provide an implantable medical device, and a method for the manufacture thereof, having a capsule, housing with a gas mixture contained therein which improves the electrical insulation properties in the interior of the device.

The above object is achieved in an implantable medical device having a capsule housing containing helium and another gas constituent which is an insulating gas or an insulating gas mixture. As used herein, "insulating" means electrically insulating.

DESCRIPTION OF THE PREFERRED EMBODIMENTS

An implantable medical device constructed in accordance with the principles of the present invention has a welded capsule housing which is filled with a gas mixture composed of helium and another gas constituent which is an insulating gas or an insulating gas mixture.

Multi-atom gases having a high electron infinity and high ionization energy are particularly well suited for use as the insulating gas. The gas constituent therefore is preferably selected from a group consisting of nitrogen, sulfur hexafluoride, carbon dioxide, oxygen or halogenated hydrocarbons such as, for example, freons. The aforementioned known gas mixture consisting of 20% helium and 80% argon has a dielectric strength of 1.3 kV/mm. A gas mixture in accordance with the principles of the present invention composed of 20% helium and 80% nitrogen has, by contrast, a dielectric strength of more than 2.5 kV/mm.

The use of such a gas mixture has the additional advantage that the implantable device can have a more compact structure, because the distance between the electrical lines and electrical components within the device can be reduced because of the improved electrical insulation in the interior of the device. Moreover, in the event that the capsule housing has one or more microscopically small leaks, the diffusion rate for the insulating gas or gas mixture through the leaks is reduced due to the use of multi-atom insulating gases, i.e., gases having large molecules, whereas the helium still enables such leaks to be found due to its extremely small molecules.

The medical device constructed in accordance with the principles of the present invention is preferably an implantable defibrillator, wherein the improved insulation properties are particularly advantageous because of the high-voltage pulses which are generated by the defibrillator. A defibrillator constructed in accordance with the principles of the present invention which delivers the same output voltage as a conventional defibrillator can be made smaller, or conversely if a defibrillator is constructed in accordance with the principles of the present invention having the same component packing density as a conventional defibrillator, the output voltage can be made higher.

A method for manufacturing an implantable medical device in accordance with the principles of the present invention includes the steps of sealing the electrical components in a capsule housing by welding two housing halves together from the exterior in a vacuum or in a protective gas atmosphere, followed by filling the interior of the capsule housing thus created with a gas mixture of helium and the aforementioned insulating gas or insulating gas mixture through an opening in the capsule housing. The opening is then subsequently hermetically closed.

The gas can be maintained in the capsule housing at an overpressure (i.e., a pressure inside the device which is higher than the ambient pressure outside of the device), so that the free propagation path of the electrons is thereby reduced, and thus the insulation properties are further improved.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable defibrillator comprising:

a welded capsule housing having a sealed interior;

a plurality of electronic components in said housing forming means for generating electrical defibrillation signals for administration to a patient; and a gas mixture in said interior composed of helium and an inert gas component, said inert gas component being selected from the group consisting of nitrogen, sulfur hexafluoride, carbon dioxide, atmospheric air, oxygen and halogenated hydrocarbons for electrically insulating said electronic components.

2. A defibrillator as claimed in claim 1 wherein said gas mixture composed of helium and an inert gas component is maintained in said capsule housing at an overpressure.

* * * * *